US012708399B2

(12) United States Patent
Golan et al.

(10) Patent No.: US 12,708,399 B2
(45) **Date of Patent: *Aug. 18, 2026**

(54) TRANSCATHETER VALVE LACERATION DEVICE AND METHOD

(71) Applicant: Pi-Cardia Ltd., Rehovot (IL)

(72) Inventors: Erez Golan, Rehovot (IL); Benzion Spector, Tel Mond (IL)

(73) Assignee: PI-CARDIA LTD., Rehovot (IL)

( * ) Notice: Subject to any disclaimer, the term of this patent is extended or adjusted under 35 U.S.C. 154(b) by 848 days.

This patent is subject to a terminal disclaimer.

(21) Appl. No.: 17/857,326

(22) Filed: Jul. 5, 2022

(65) Prior Publication Data

US 2023/0010485 A1 Jan. 12, 2023

Related U.S. Application Data

(60) Provisional application No. 63/220,588, filed on Jul. 12, 2021.

(51) Int. Cl.

*A61B 17/3207* (2006.01)
*A61F 2/24* (2006.01)
*A61B 17/00* (2006.01)

(52) U.S. Cl.

CPC .... *A61B 17/320725* (2013.01); *A61F 2/2427* (2013.01); *A61B 2017/00783* (2013.01)

(58) Field of Classification Search

CPC ........ A61B 17/22031; A61B 17/22004; A61B 17/22012; A61B 17/3207; A61B 17/20725; A61B 2017/00243; A61B 2017/22098; A61B 17/320725; A61F 2/24; A61F 2/2427

See application file for complete search history.

(56) References Cited

U.S. PATENT DOCUMENTS

| | | | | |
|---|---|---|---|---|
| 5,047,041 | A | 9/1991 | Samuels | |
| 5,613,937 | A | 3/1997 | Garrison et al. | |
| 6,830,584 | B1 | 12/2004 | Seguin | |
| 9,364,255 | B2 * | 6/2016 | Weber | A61B 17/320725 |
| 2004/0034380 | A1 | 2/2004 | Woolfson et al. | |
| 2005/0131438 | A1 | 6/2005 | Cohn | |
| 2005/0203549 | A1 | 9/2005 | Realyvasquez | |
| 2007/0185513 | A1 | 8/2007 | Woolfson et al. | |
| 2010/0076476 | A1 | 3/2010 | To et al. | |
| 2010/0286719 | A1 | 11/2010 | Paul et al. | |
| 2013/0066346 | A1 | 3/2013 | Pigott | |
| 2013/0116715 | A1 | 5/2013 | Weber | |
| 2015/0359556 | A1 | 12/2015 | Vardi | |
| 2016/0100855 | A1 | 4/2016 | Lemaitre et al. | |

(Continued)

FOREIGN PATENT DOCUMENTS

| | | |
|---|---|---|
| AU | 2006211174 | 8/2006 |
| CN | 1418074 | 5/2003 |

(Continued)

*Primary Examiner* — Sarah W Aleman
(74) *Attorney, Agent, or Firm* — PEARL COHEN LLP

(57) ABSTRACT

A transcatheter valve laceration device includes a leaflet support frame and a leaflet cutting assembly, both of which are movably mounted on a guiding structure and movable between contracted and expanded orientations. In the expanded orientation, a blade protector of the leaflet support frame is positioned over a cutting element of the leaflet cutting assembly.

5 Claims, 15 Drawing Sheets

(56) References Cited

U.S. PATENT DOCUMENTS

| | | | |
|---|---|---|---|
| 2016/0166243 | A1 | 6/2016 | Wilson et al. |
| 2017/0209160 | A1 | 7/2017 | Pigott |
| 2018/0000509 | A1 | 1/2018 | Wilson et al. |
| 2018/0064460 | A1 | 3/2018 | Vardi et al. |
| 2018/0092661 | A1 | 4/2018 | Prabhu |
| 2019/0029790 | A1 | 1/2019 | Bak-Boychuk et al. |
| 2019/0069920 | A1* | 3/2019 | Astarci .......... A61B 17/320725 |
| 2019/0209315 | A1 | 7/2019 | Zhang et al. |
| 2019/0298517 | A1 | 10/2019 | Sanchez et al. |
| 2020/0289102 | A1* | 9/2020 | Wilson ........... A61B 17/320016 |
| 2021/0085456 | A1* | 3/2021 | Skarsgard .......... A61B 17/3423 |

FOREIGN PATENT DOCUMENTS

| | | |
|---|---|---|
| CN | 102985018 | 3/2013 |
| CN | 104812318 | 7/2015 |
| CN | 109561891 | 4/2019 |

* cited by examiner 10
14
12
16
24
36
14
38
49
26
40
30
18
21
12
45
22
32
50
44
32
19
20
28

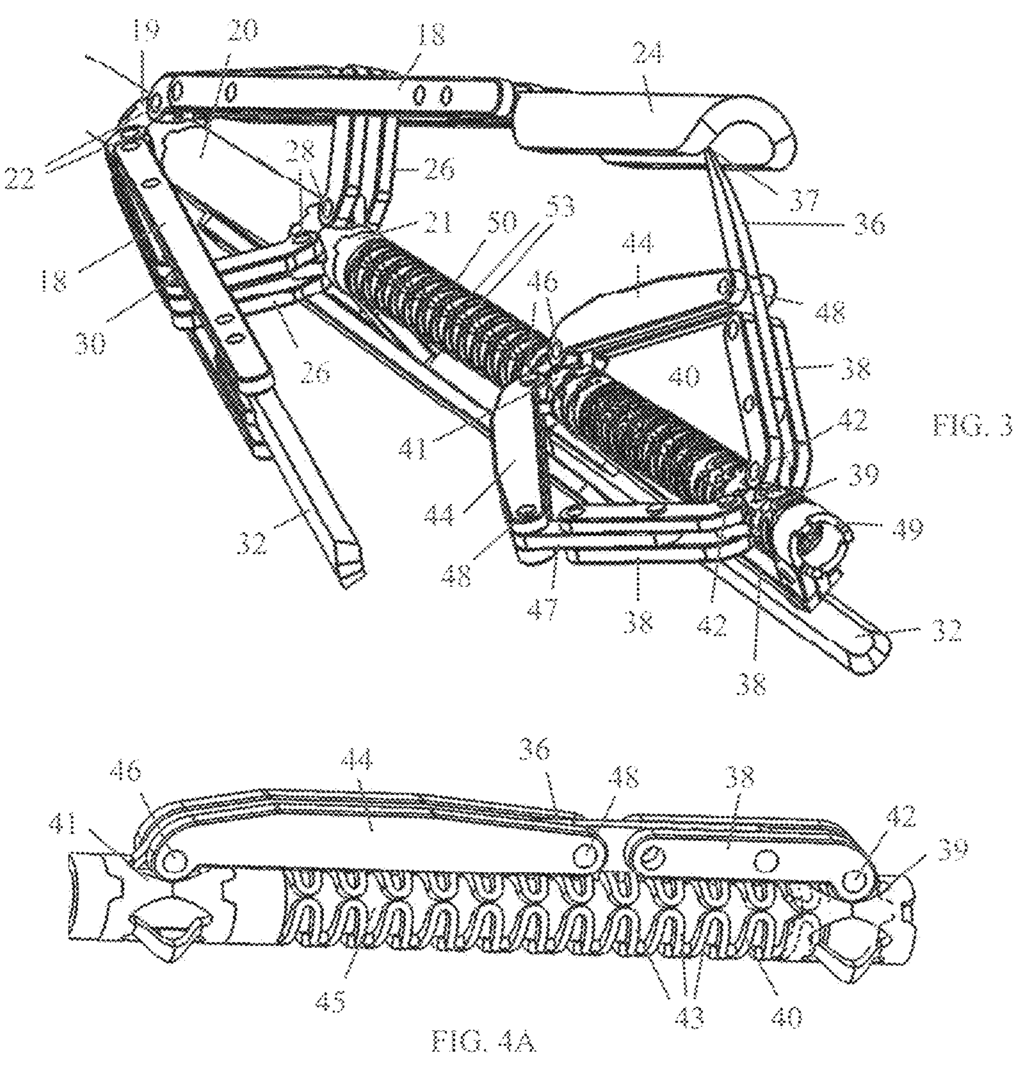
FIG. 3
FIG. 4A
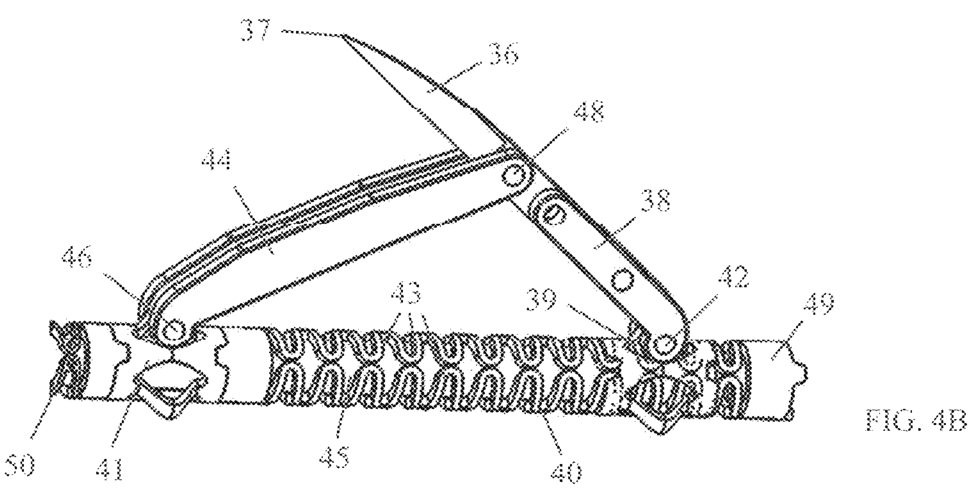
FIG. 4B 51
54
14
12
16
10

51
24
10
12

18
50
14
24
18
12
10

50
18
32

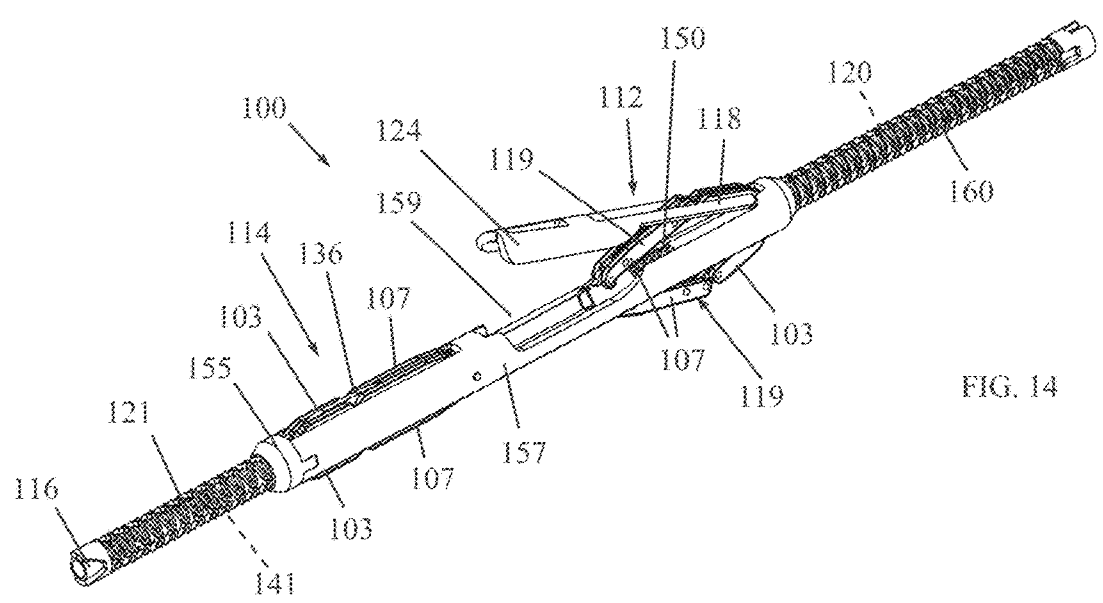
FIG. 14
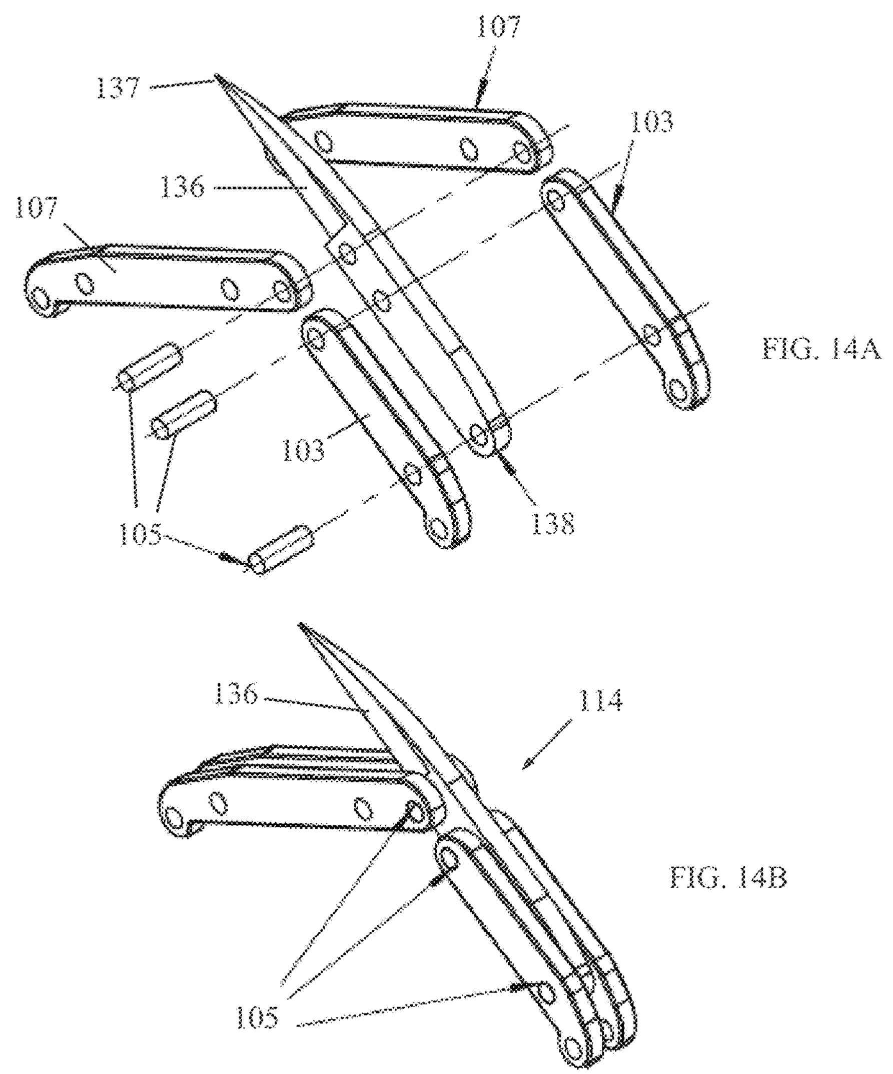
FIG. 14A
FIG. 14B

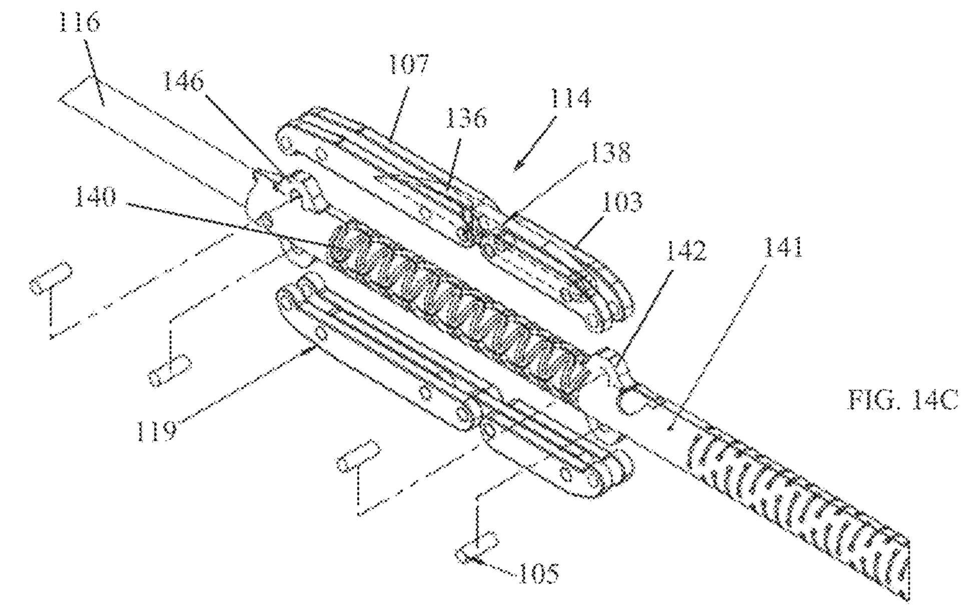
FIG. 14C
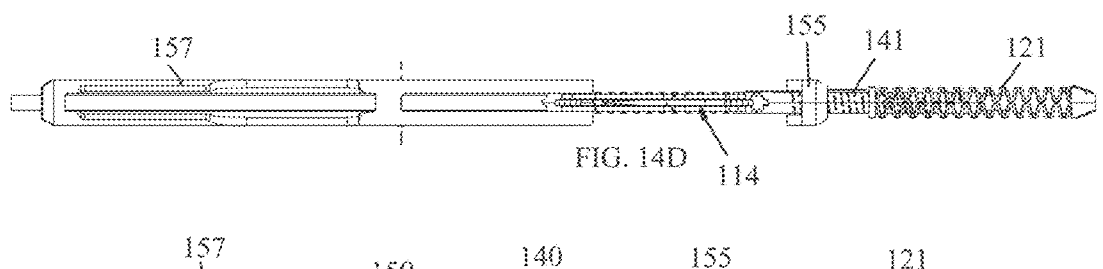
FIG. 14D
FIG. 14E
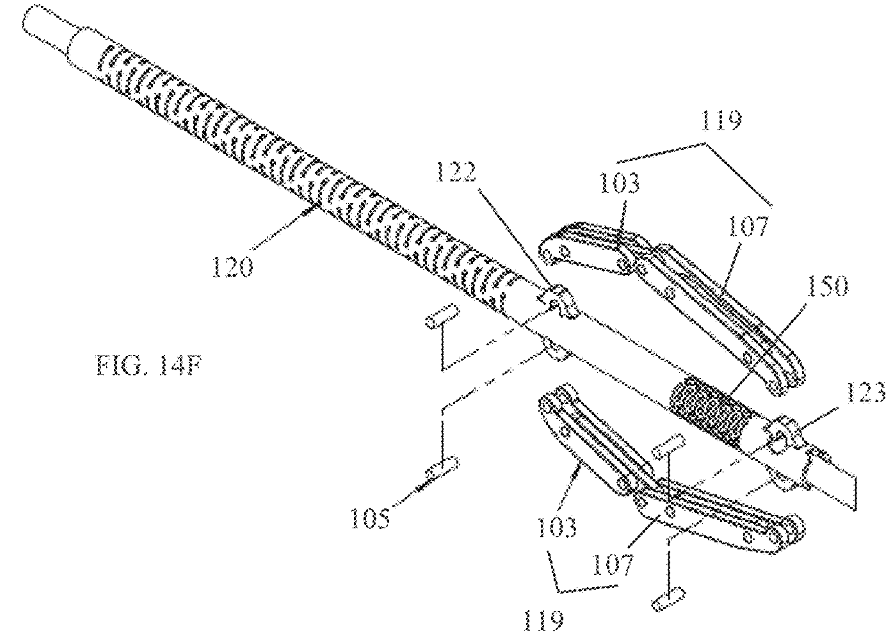
FIG. 14F

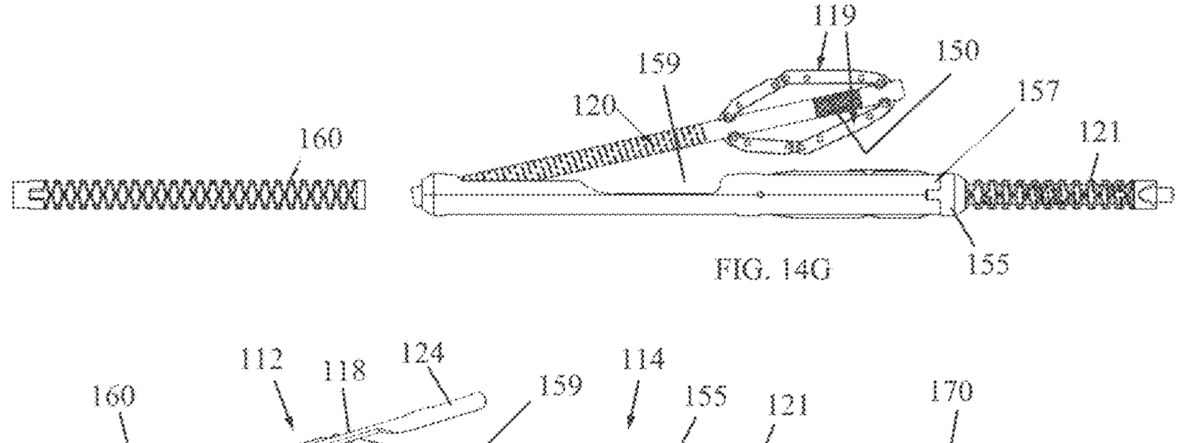
FIG. 14G
FIG. 14H
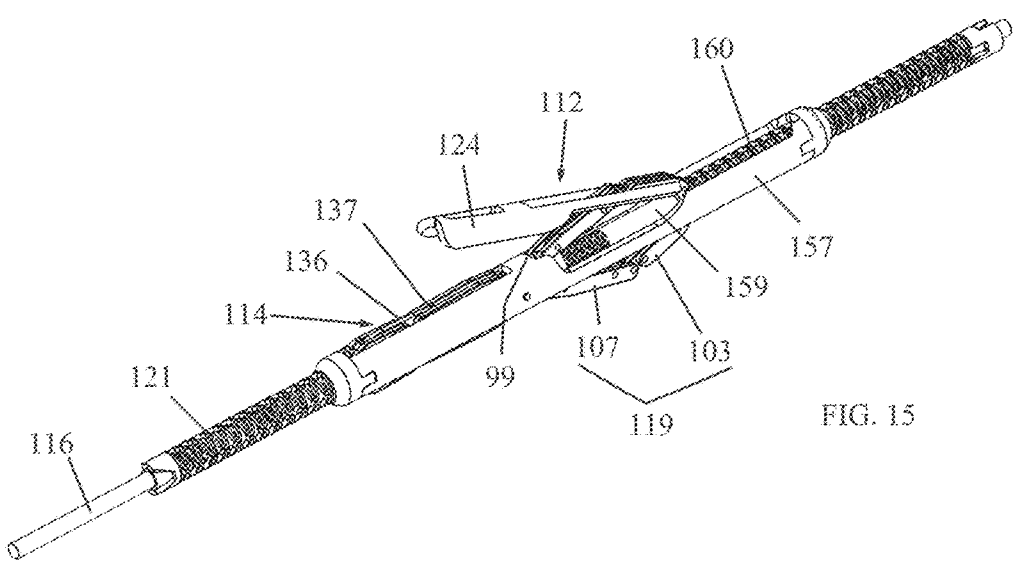
FIG. 15

TRANSCATHETER VALVE LACERATION DEVICE AND METHOD

CROSS-REFERENCE TO OTHER APPLICATIONS

This application claims priority from U.S. Provisional Patent Application 63/220,588, filed July 7, 2021 which is incorporated herein by reference in its entirety.

FIELD OF THE INVENTION

The present invention generally relates to devices and methods for transcatheter laceration of heart valve leaflets, such as aortic leaflets.

BACKGROUND OF THE INVENTION

PCT Patent Application PCT/IB2020/054729 describes a transcatheter valve laceration device and method. The invention is a method and device, which can be used to perform BASILICA (Bioprosthetic or native Aortic Scallop Intentional Laceration to prevent Iatrogenic Coronary Artery obstruction). The device is a cutting device with attention to preventing damage to neighboring tissues. The device can be implemented in other cardiologic procedures, such as tricuspidization of a bicuspid valve (turning a bicuspid valve into a tricuspid valve by cutting or splitting one of the bicuspid leaflets into two leaflets) or tricuspidization of a quadricuspid valve (lacerating one of the leaflets to turn the valve into a tricuspid valve), thereby preparing the patient for safe transcatheter aortic valve replacement (TAVR), or for other procedures that involve cutting cardiac tissue.

SUMMARY OF THE INVENTION

The present invention seeks to provide a method for performing mitral anterior leaflet laceration for transcatheter mitral valve replacement (TMVR) procedure to prevent LVOT (left ventricle outflow tunnel) obstruction when the implant valve is positioned within the native valve of the patient.

The invention uses the same device described in PCT Patent Application PCT/IB2020/054729, and now commercially available as ShortCut™ from Pi-Cardia Ltd., Rehovot, Israel.

In accordance with a non-limiting embodiment of the present invention, the transcatheter valve laceration device includes a cutting element mounted on a guiding structure. The cutting element is expandable and contractible with respect to the guiding structure. The guiding structure is deliverable to a heart valve and the cutting element is expanded and moved (in a direction which may be different than the expansion direction) towards the valve leaflets to cut them. A support structure may be provided on the opposite side of the valve leaflets to act as an "anvil" against the cutting force of the cutting element and to protect tissues, which should not be cut, from the cutting element.

BRIEF DESCRIPTION OF THE DRAWINGS

The present invention will be understood and appreciated more fully from the following detailed description, taken in conjunction with the drawings in which:

FIG. 3 is another view of the deployed orientation;

FIGS. 4A and 4B are simplified pictorial illustrations of the leaflet cutting assembly, in respective stowed (contracted) and deployed (expanded) orientations;

FIGS. 6A and 6B are simplified pictorial illustrations, at different perspective views, of the delivery system after unsheathing;

FIGS. 7A and 7B are simplified pictorial illustrations of a leaflet support frame of the device being deployed, in which FIG. 7A shows the deployment in-situ at the valve site and FIG. 7B shows the device itself deployed;

FIG. 8 is a simplified pictorial illustration of the leaflet support frame and a leaflet cutting assembly deployed in-situ at the valve site;

FIGS. 9A-9E are simplified pictorial illustrations of a method of using the transcatheter valve laceration device to lacerate aortic valve leaflets, wherein:

FIG. 9A is a simplified pictorial illustration of the transcatheter valve laceration device introduced and positioned in its contracted orientation at the aortic valve;

FIG. 9B is a simplified pictorial illustration of the leaflet support frame being deployed (expanded) on one side of the aortic valve and the leaflet cutting assembly still in the contracted orientation in the aortic valve;

FIG. 9C is a simplified pictorial illustration of the leaflet support frame expanded and positioned against one side of the aortic valve and the leaflet cutting assembly still in the contracted orientation on the other side of the aortic valve;

FIG. 9D is a simplified pictorial illustration of the leaflet cutting assembly being deployed and expanded radially outwards;

FIG. 9E is a simplified pictorial illustration of the leaflet cutting assembly being moved axially to cut the leaflets;

FIG. 14 is a simplified pictorial illustration of a transcatheter valve laceration device, constructed and operative in accordance with another non-limiting embodiment of the invention;

FIGS. 14A and 14B are simplified exploded and pictorial illustrations, respectively, of a leaflet cutting assembly of the device of FIG. 14;

FIG. 14C is a simplified pictorial illustration of the leaflet cutting assembly pivotally coupled to opposite ends of a first biasing device at pivot joints;

FIGS. 14D and 14E are simplified pictorial illustrations of the leaflet cutting assembly assembled with a distal spring and a frame;

FIG. 14F is a simplified exploded illustration of a leaflet support frame of the device of FIG. 14;

FIG. 14G is a simplified pictorial illustration of the leaflet support frame being mounted in the frame;

FIG. 14H is a simplified pictorial illustration of the finished device with a blade protector;

FIG. 15 is a simplified pictorial illustration of the leaflet support frame moved distally towards the leaflet cutting assembly and the leaflet support frame has been expanded radially outwards;

DETAILED DESCRIPTION OF EMBODIMENTS

Figures 1, 2:
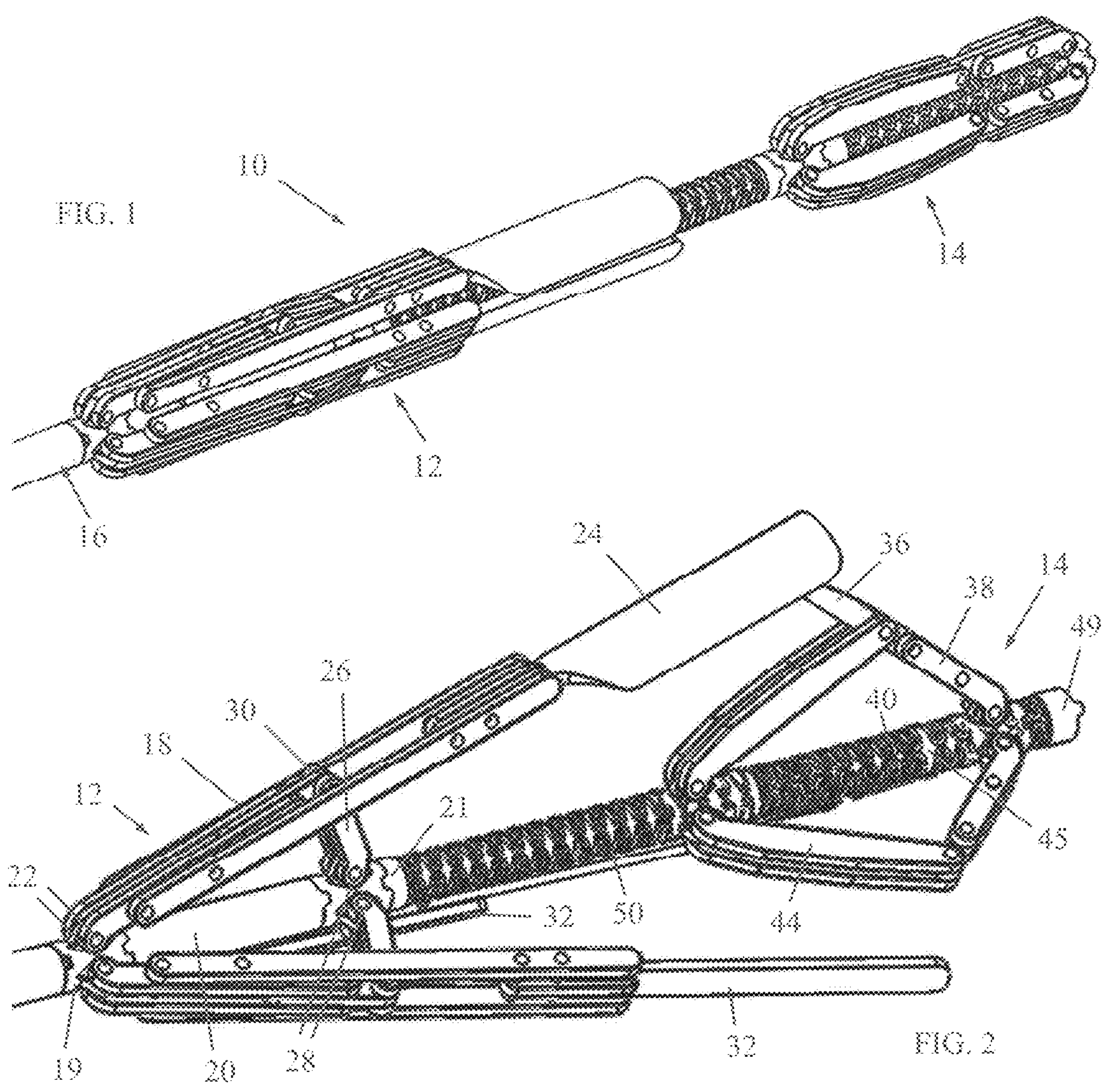
FIG. 1 is a simplified pictorial illustration of a transcatheter valve laceration device, constructed and operative in accordance with a non-limiting embodiment of the invention, in a stowed (contracted) orientation for deployment to the surgical site.
FIG. 2 is a simplified pictorial illustration of the transcatheter valve laceration device in a deployed (expanded) orientation, this orientation being used to lacerate valves in-situ.

Reference is now made to FIGS. 1-3, which illustrate a transcatheter valve laceration device 10, constructed and operative in accordance with a non-limiting embodiment of the invention.

Device 10 includes a leaflet support frame 12 and a leaflet cutting assembly 14, both of which are mounted on a guiding structure 16 (FIG. 1).

In the illustrated embodiment of FIGS. 2 and 3, leaflet support frame 12 includes a strut arm 18, one end of which is pivotally coupled to a first portion 19 of a support frame tube 20 (which is part of the guiding structure 16) at a pivot joint 22, and an opposite end of which is coupled to a blade protector 24. The blade protector 24 may be shaped as a semi-hemispherical tube. Strut arm 18 and blade protector 24 may be collinear or may be tilted with respect to each other. An actuator arm 26 has one end pivotally coupled to a second portion 21 of support frame tube 20 at a pivot joint 28 and an opposite end pivotally coupled to strut arm 18 at a pivot joint 30.

In the illustrated embodiment of FIGS. 2 and 3, there is more than one strut arm 18 (three are shown spaced 120° apart, but there could be one, two or any other number, not necessarily spaced symmetrically about the guiding structure). Only one of the strut arms 18 is coupled to blade protector 24 (since there is only one cutting element); each of the other strut arms 18 is coupled to a positioning member 32 which does not need to protect any tissue from a cutting element but may be useful in properly positioning, self-centering and aligning the leaflet support frame 12 with respect to the valve structure. Strut arm 18 may have a double-arm construction, in which two parallel arms are used; the actuator arm 26 is positioned between the parallel arms and is pivotally coupled to both of them with pivot joint 30.

In the illustrated embodiment of FIGS. 2 and 3, leaflet cutting assembly 14 includes a cutting element 36 that extends from a blade arm 38. Cutting element 36 and blade arm 38 may be collinear or may be tilted with respect to each other. Cutting element 36 has a pointed, sharp tip 37. The blade arm 38 has one end pivotally coupled to a first portion 39 of a first biasing device 40 (which is part of the guiding structure 16) at a pivot joint 42. A blade actuator arm 44 has one end pivotally coupled to a separator tube 41 at a pivot joint 46 and an opposite end pivotally coupled to blade arm 38 at a pivot joint 48. The separator tube 41 separates first biasing device 40 from a second biasing device 50. The second biasing device 50 extends from the second portion 21 of support frame tube 20 to the separator tube 41.

In the illustrated embodiment of FIGS. 2 and 3, there is more than one blade arm 38 (three are shown spaced 120° apart, but there could be one, two or any other number, not necessarily spaced symmetrically about the guiding structure). Only one cutting element 36 is coupled to one of the blade arms 38, but in other embodiments more than one cutting element 26 may be used. Blade arm 38 may have a double-arm construction, in which two parallel arms are used and an auxiliary arm 47 (FIG. 3), instead of cutting element 36, is positioned between the parallel arms and is pivotally coupled to blade actuator arm 44 with pivot joint 48. Blade actuator arm 44 may also have a double arm construction (two parallel arms).

Reference is now made to FIGS. 4A and 4B. In FIG. 4A, the leaflet cutting assembly 14 is in a stowed (contracted) orientation. In this orientation, the cutting element 36 lies between the double arms of blade actuator arm 44. Thus, the blade actuator arm 44 serves as a cutting element protector in the stowed position of the device, protecting delicate tissues from being accidentally cut by the cutting element 36. The first biasing device 40 may be constructed of a repetitive series of arcuate (e.g., wavy or sinusoidal) elements 43 that are wrapped at least partially around an actuator tube 45.

In the illustrated embodiment, there are two or more rows of arcuate elements 43; the rows together wrap around the circumference of tube 45. The arcuate elements 43 may be made of an elastic material, such as nitinol, and may have a constant spring force. In the stowed position, the arcuate elements 43 of first biasing device 40 are in tension and exert a tensile force on blade arm 38 and actuator arm 44 to keep them in the stowed position, such that they are normally "closed" (i.e., in the collapsed orientation).

The actuator tube 45 has a distal cap 49 against which the most distal arcuate element 43 abuts. The actuator tube 45 is movable axially with respect to support frame tube 20 (FIG. 2), wherein actuator tube 45 may slide inside support frame tube 20.

Similarly to the first biasing device 40, the second biasing device 50 may be constructed of a repetitive series of arcuate (e.g., wavy or sinusoidal) elements 53 (FIG. 3) that are wrapped at least partially around tube 20. The spring force of the first biasing device 40 is greater than the spring force of the second biasing device 50 (such as a ratio of 4:1, although the invention is not limited to this ratio).

In FIG. 4B, the leaflet cutting assembly 14 is in a deployed (expanded) orientation. This may be achieved by moving actuator tube 45 proximally (towards leaflet support frame 12). This action compresses the arcuate elements 43 of biasing device 40. Blade actuator arm 44 is now tilted with respect to tube 45 (arms 38 and 44 and tube 45 form a triangular construction) and serves as a guidance surface for leaflet tissue to slide thereupon towards the sharp tip 37 (and edge) of cutting element 36.

Accordingly, the guiding structure 16 includes tubes 20 and 45.

Figure 5A:
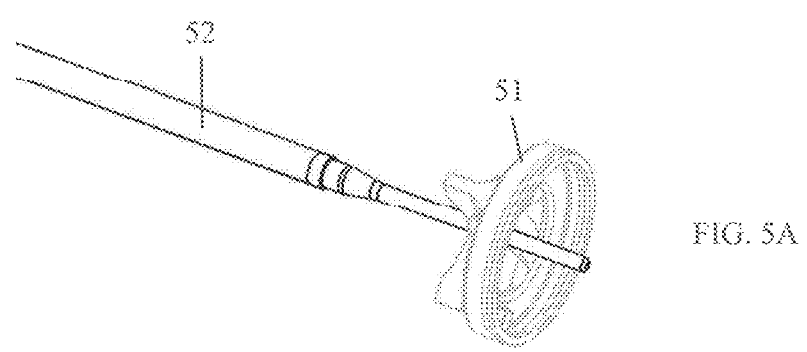
FIGS. 5A and 5B are simplified pictorial illustrations of the sheathed delivery system, respectively during and after introduction into the aortic valve.
Figure 5B:
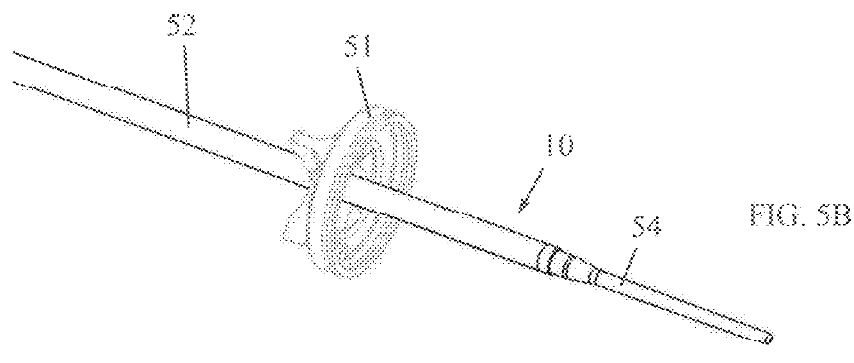

Reference is now made to FIGS. 5A and 5B, which illustrate the transcatheter valve laceration device 10 enclosed in a sheath 52, respectively during and after introduction into the aortic valve 51. In FIGS. 5A and 5B, the left side of aortic valve 51 is the aorta side and the right side is the left ventricle side.

Figure 6A:
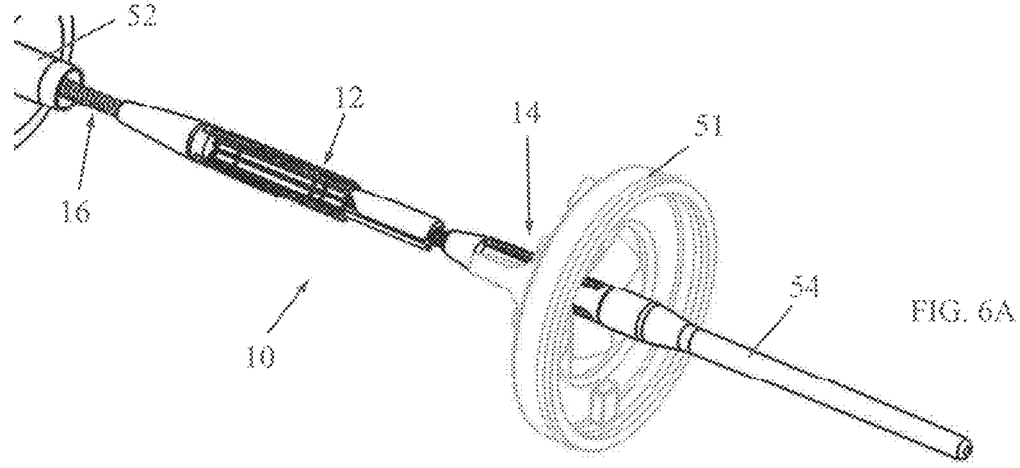
Figures 6B, 7A, 7B:
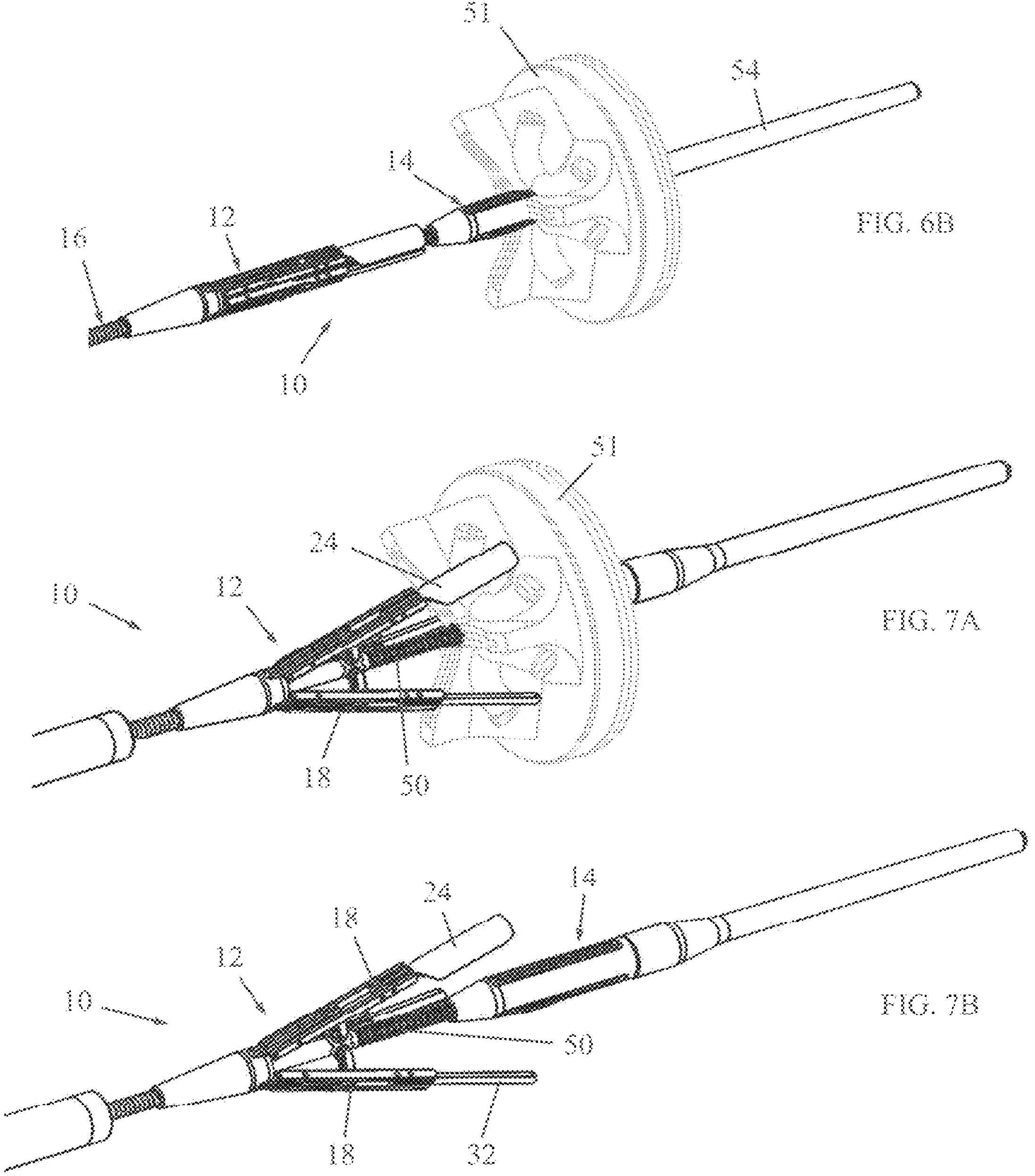

FIGS. 6A and 6B illustrate the delivery system after unsheathing (moving sheath 52 proximally). The device 10 may include a smooth portion 54 distal to leaflet cutting assembly 14.

Reference is now made to FIGS. 7A and 7B, which illustrate leaflet support frame 12 being deployed. FIG. 7A shows the device deployed in-situ at the valve site and FIG. 7B shows the device deployed with the valve omitted. The deployment is achieved by moving the actuator tube 45 (FIGS. 2 and 3) proximally towards the leaflet support frame 12. Due to the fact that the spring force of the first biasing device 40 is greater than the spring force of the second biasing device 50, as mentioned above, the proximal movement of the actuator tube 45 first compresses the weaker second biasing device 50 without compressing the stronger first biasing device 40. The proximal movement of the actuator tube 45 causes the actuator arms 26 (FIGS. 2 and 3) to move radially outwards, thereby deploying the strut arms 18 and blade protector 24 radially outwards. The first biasing device 40 is not yet compressed so the cutting elements 36 remain in the closed, stowed position.

Figures 8, 9A, 9B:
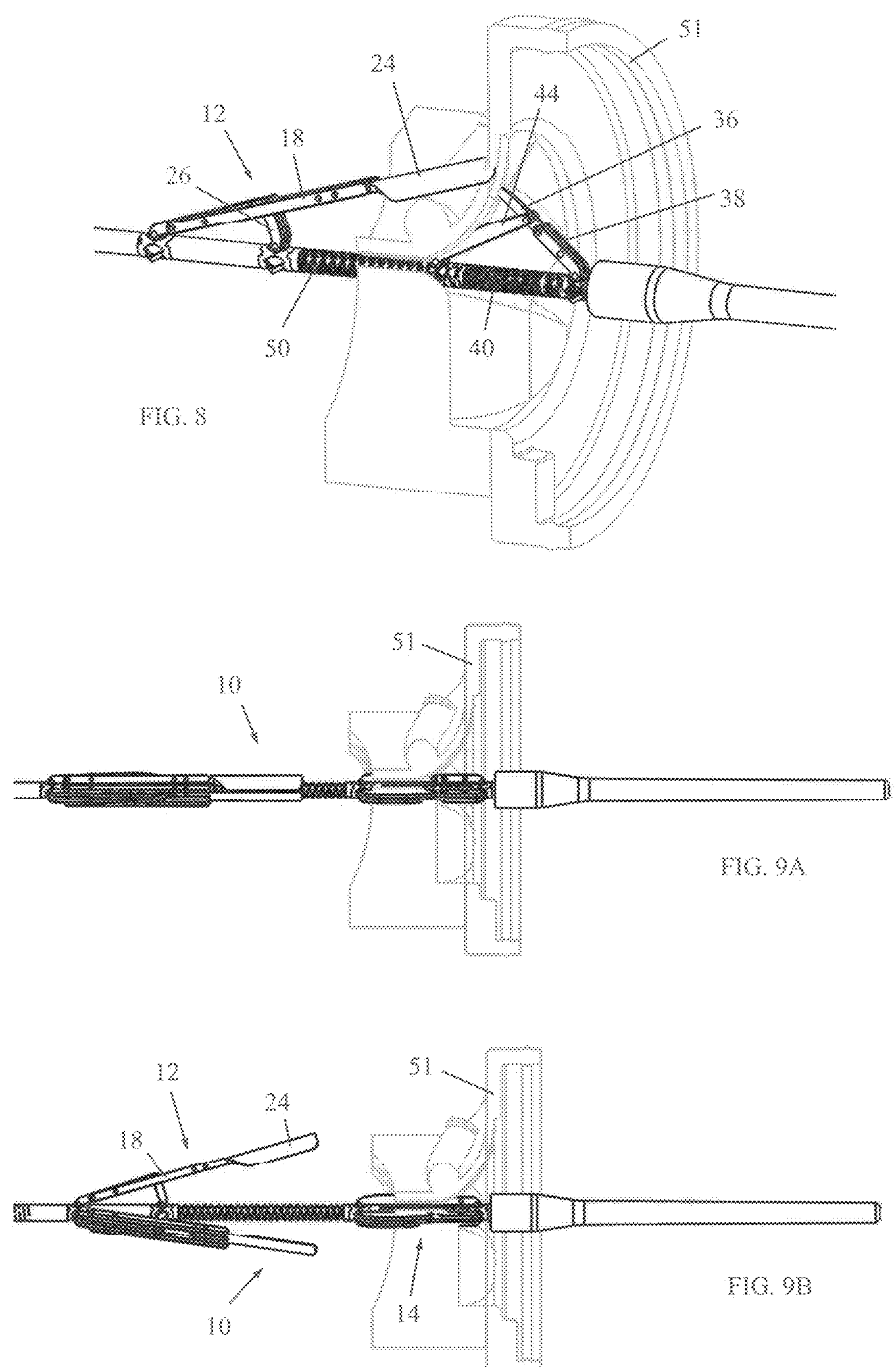

Reference is now made to FIG. 8. Further proximal movement of the actuator tube 45 now compresses the first biasing device 40. This further movement of the actuator tube 45 causes deployment of blade actuator arm 44, which in turn deploys blade arm 38 and cutting element 36, expanding them radially outwards against the leaf tissue of the aortic valve 51. The sharp distal tip 37 of the cutting element 36 pierces the leaf tissue.

Reference is now made to FIGS. 9A-9E, which illustrate a method of using the transcatheter valve laceration device 10 to lacerate aortic valve leaflets.

In FIG. 9A, device 10 is introduced and positioned in its contracted orientation at the aortic valve 51.

In FIG. 9B, the leaflet support frame 12 is deployed (expanded) on one side (aorta side) of the aortic valve and the leaflet cutting assembly 14 is still in the contracted orientation in the aortic valve 51.

Figure 9C:
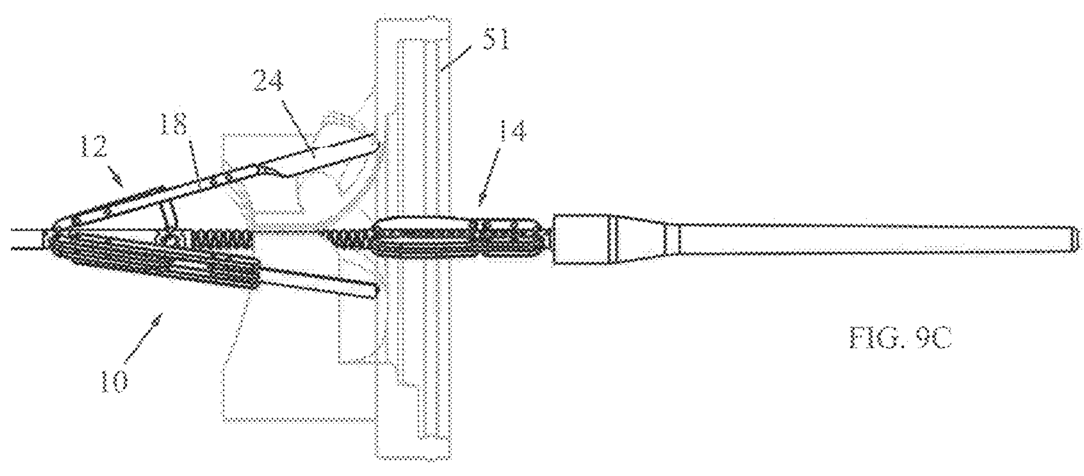

In FIG. 9C, the leaflet support frame 12 expanded and positioned against one side (aorta side) of the aortic valve 51 and the leaflet cutting assembly 14 is still in the contracted orientation on the other side (left ventricle side) of the aortic valve 51.

Figure 9D:
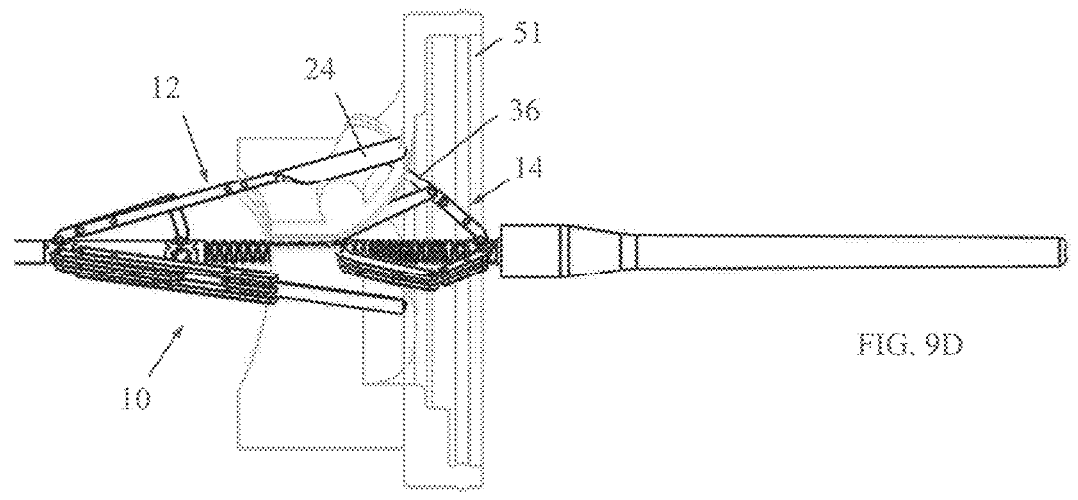

In FIG. 9D, the leaflet cutting assembly 14 is deployed and expanded radially outwards.

Figure 9E:
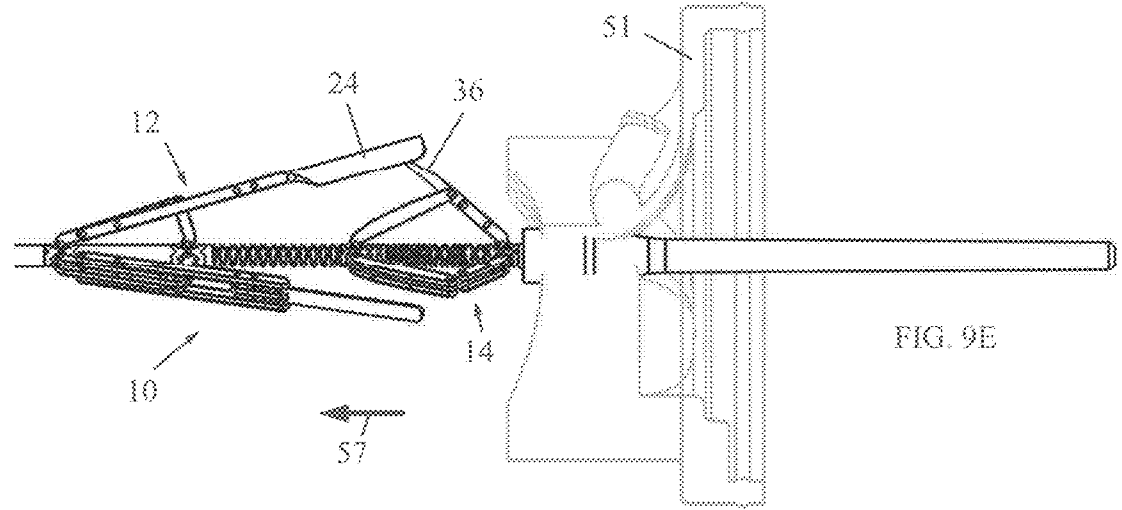

In FIG. 9E, the leaflet cutting assembly 14 is moved axially (in the proximal direction 57) to cut one or more leaflets.

After completing the procedure, actuator tube 45 is moved distally to contract the leaflet cutting assembly 14 and the leaflet support frame 12. The biasing force of the first biasing device 40 helps contract the leaflet cutting assembly 14. The biasing force of the second biasing device 50 helps contract the leaflet support frame 12.

In summary, with three strut arms and three blade arms, the device 10 may have a triangular tripod construction for cutting element activation in which axial movement is translated into tripod expansion movement. The symmetrical spacing of the strut arms provides self-positioning of the device onto the valve cusps. The support frame construction allows blade penetration and protection of adjacent tissue by ensuring that the sharp tip of the blade (cutting element) expands to be underneath the blade protector. The blade action punctures through the aortic valve leaflet and then dissects the leaflet by an axial proximal movement (pull) of the frame and the blade structure that forces the leaflet centerline to be split by the sharp blade. The fully hinged mechanism allows folding of the mechanism to be sheathed into a delivery system catheter tube. Other embodiments may be based on other radial and non-radial flexing methods.

Single or multiple protector elements and blades may be used. Constant force biasing devices preload the mechanism to keep it normally closed (collapsed).

Leaflet puncturing is performed from within the left ventricle with a circular rising movement of the blade tip towards the convex side of the leaflet. In this manner, the cutting element punctures through the leaflet while the blade protector ensures the cutting element tip does not extend to the aorta and thus prevents damage to the aortic complex. The support frame deployment and positioning may be performed within the sinotubular junction (STJ) volume, and there is minimal contact with adjacent elements in the aortic complex.

An embodiment of the support frame construction may include features and struts to prevent full valve leaflet closure during dissection action. This is done in order to ensure complete dissection of the valve leaflets along its axial direction.

Figure 10:
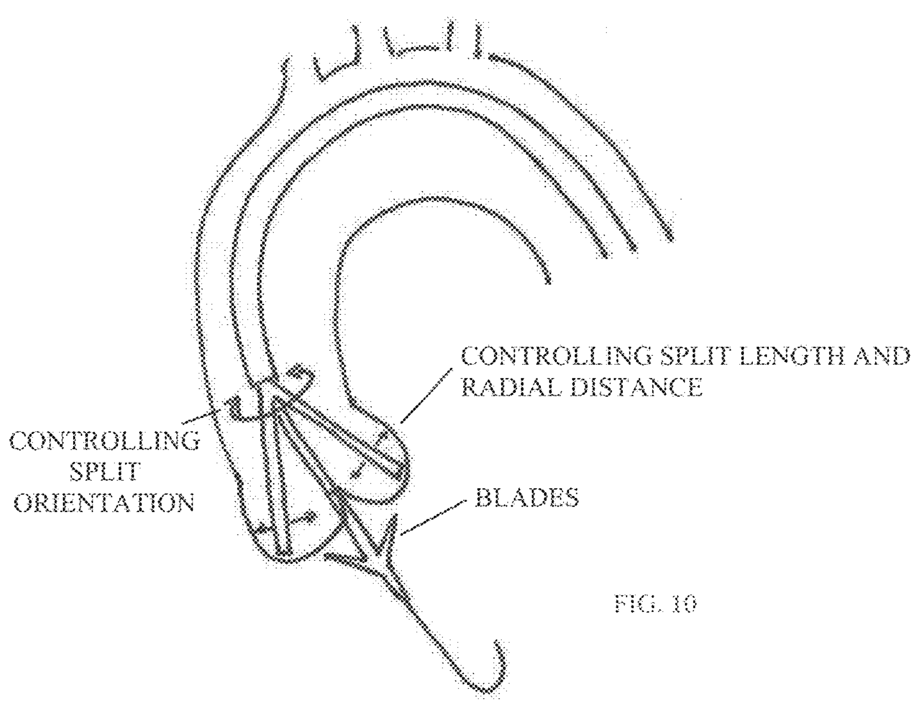
FIG. 10 is a simplified pictorial illustration of a transcatheter valve laceration device, constructed and operative in accordance with another non-limiting embodiment of the invention.

Reference is now made to FIG. 10, which illustrates a transcatheter valve laceration device, constructed and operative in accordance with another non-limiting embodiment of the invention. The device includes one or more tissue laceration elements configured to extend radially from a contracted position (during delivery to the target site) to an expanded position (during the laceration action).

The laceration device includes support elements deployable in the aortic (downstream) side of the aortic valve, and cutting blades positioned in the ventricular side of the valve—specifically in the outflow tract. The support elements can be radially controlled to land in the aortic sinuses in such a way that defines the split length and radial length of the cut. In addition, the orientation of the cut vis-à-vis the centerline of the leaflet can be adjusted.

Figure 11:
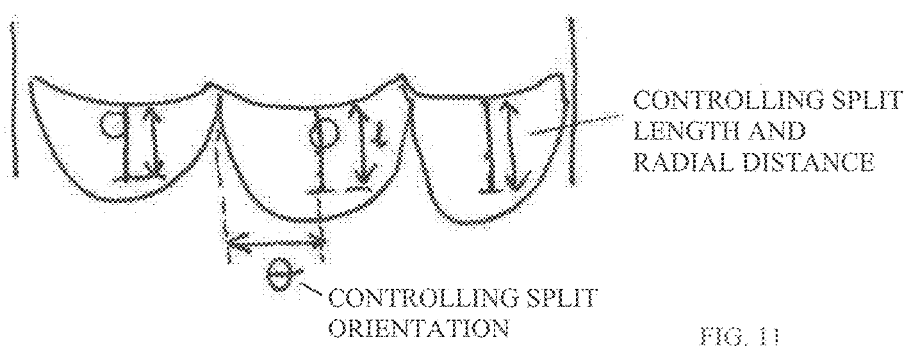
FIG. 11 is a simplified pictorial illustration of a flattened aortic valve showing the control ability of the laceration device and its ability to control the location where the cutting elements will start cutting the leaflet tissue.

FIG. 11 is an illustration of a flattened aortic valve showing the control ability of the laceration device and its ability to control the location where the cutting elements will start cutting the leaflet tissue. By adjustment of the support element's degree of radial expansion, the depth in which the cutting elements punch through the leaflet on the ventricular side can be controlled. Moreover, the rotational position of the support arms can be adjusted to cut "off-center" should multiple cuts be needed.

Figure 12A:
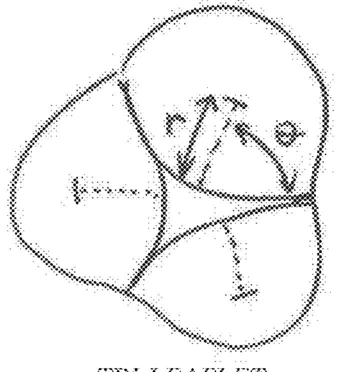
FIG. 12A is a simplified pictorial illustration of a tricuspid aortic native valve complex, wherein Θ represents the angle defining the distance from the native commissures to the location of the desired cut.

FIG. 12A is a schematic illustration of a tricuspid aortic native valve complex. Θ represents the angle defining the distance from the native commissures to the location of the desired cut. By manipulating Θ, the length of the cut "r" is also defined.

Figure 12B:
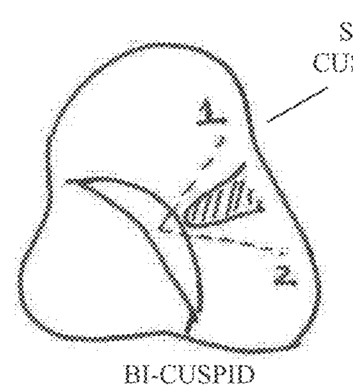
FIG. 12B is a simplified pictorial illustration of a bicuspid aortic native valve complex.

FIG. 12B is a schematic illustration of a bicuspid aortic native valve complex. The hashed area represents the raphe—a thickened area located roughly in the center of the larger of the two leaflets. The shape and thickness of the raphe often affect degree and progression of valvular degeneration. FIG. 12B shows two dotted lines representing lengthwise cuts designed to release the area around the raphe to facilitate the implantation of a prosthetic valve.

Figure 13A:
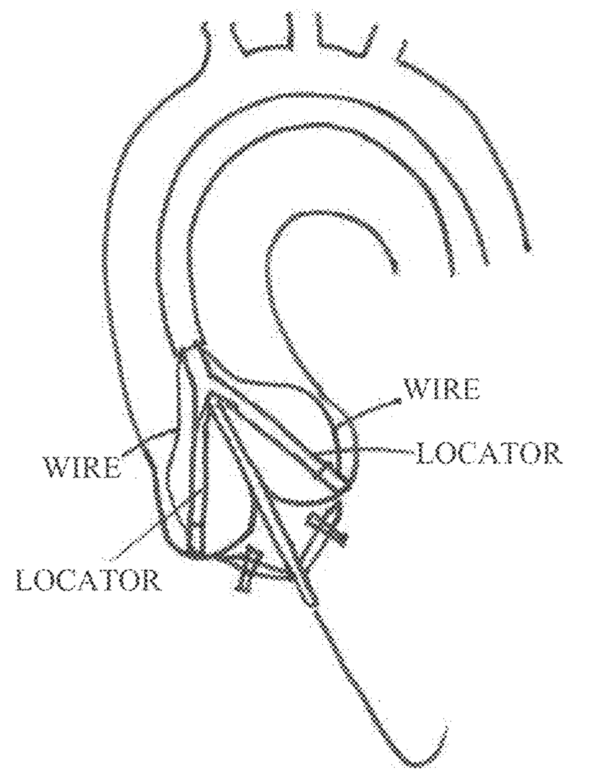
FIGS. 13A-13G are simplified pictorial illustrations of a method of lacerating the tissue of a native valve as a precursor to TAVI, in accordance another non-limiting embodiment of the invention.

FIGS. 13A-13G illustrate a method of lacerating the tissue of a native valve as a precursor to TAVI. FIG. 13A illustrates the tissue laceration device introduced into the native valve complex such that the support element is located and set at a certain orientation on the arterial side of the valve leaflets, being generally placed in the Valsalva sinuses. The laceration element is placed in the ventricular outflow tract so that the one or more laceration tacks (cutting elements) face the native leaflets.

Figure 13B:
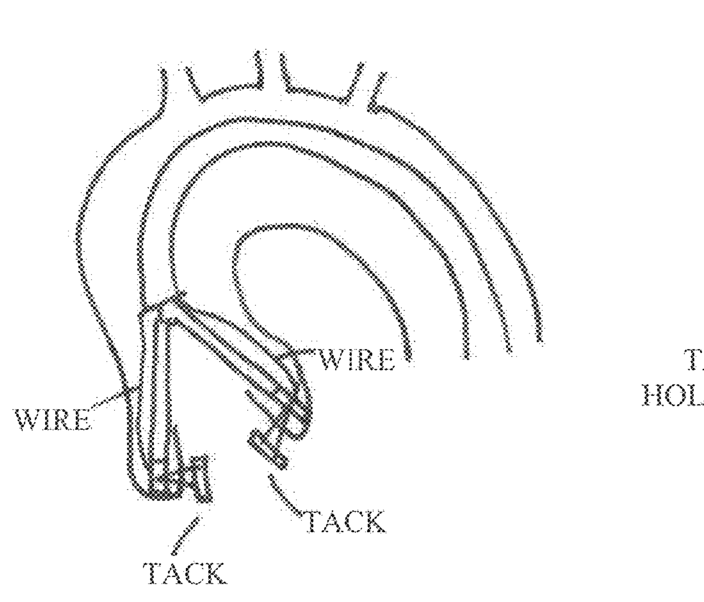

FIG. 13B is an illustration of the tacks inserted through the tissue of the leaflets and into corresponding tack holders within the support element arms. The support element is then retracted while the tacks remain embedded in the leaflet tissue with their tips firmly secured to the tack holders.

Figure 13C:
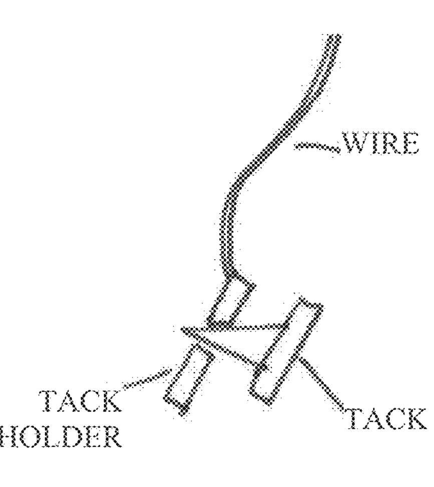

FIG. 13C is an enlarged view of the tacks embedded in the leaflets, with their tips secured within the tack holders.

Figure 13D:
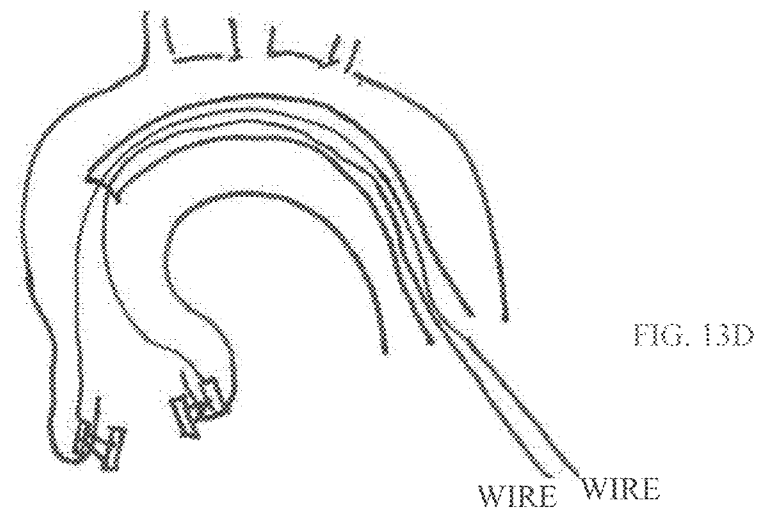

FIG. 13D shows the laceration apparatus left in place within the native valve complex, tethered by separate wires to an external handle (not shown).

Figure 13E:
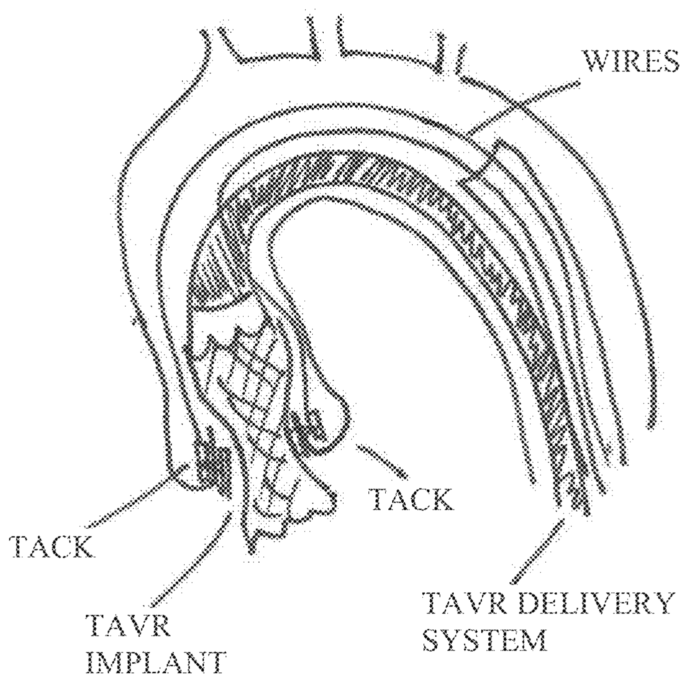

FIG. 13E shows the implantation process of a self-expanding TAVI valve (a self-expanding valve is shown, but any TAVI device can be used). The valve is still partly captured by its delivery system, which is shown in a partially open state. The surgeon can position the prosthetic valve at the desired location before lacerating the native valve leaflets, prior to full release of the prosthetic valve.

Figure 13F:
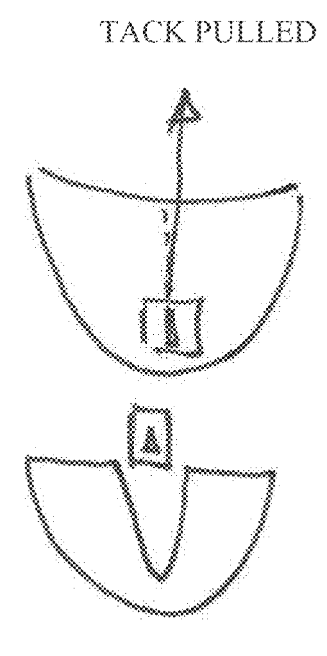

FIG. 13F illustrates a native valve leaflet with the laceration tack embedded therein before and after the laceration operation. As can be seen, the native leaflet is cut lengthwise. The cutting step is performed by pulling on the external ends of the wires tethering the tacks. By pulling the wires, the tacks and their tack holders move cranially and cut through the calcified native leaflets.

Figure 13G:
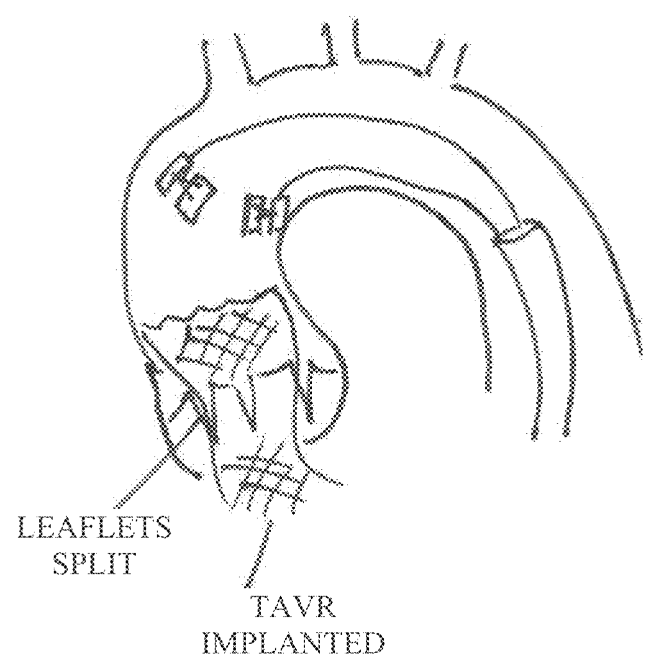

FIG. 13G illustrates the final step of TAVI, in which the prosthesis is fully released following the laceration step.

Reference is now made to FIG. 14, which illustrates a transcatheter valve laceration device 100, constructed and operative in accordance with a non-limiting embodiment of the invention. Device 100 is similar to device 10 but there are differences as described below.

Device 100 includes a leaflet support frame 112 and a leaflet cutting assembly 114, both of which are mounted on a guiding structure 116 (FIG. 14). Sub-assemblies of the device 100 of FIG. 14 are now described with reference to FIGS. 14A-14H.

As seen in FIGS. 14A and 14B, leaflet cutting assembly 114 includes a cutting element 136 that extends from a blade arm 138. Cutting element 136 and blade arm 138 may be collinear or may be tilted with respect to each other. Cutting element 136 has a pointed, sharp tip 137. The blade arm 138 may be secured to a first blade support arm 103 (in the illustrated embodiment it is secured to a pair of first blade support arms 103), such as by pins 105 or other method. The blade arm 138 may be pivotally coupled to a second blade support arm 107 (in the illustrated embodiment it is pivotally coupled to a pair of second blade support arms 107), such as by another pin 105 or other method.

The assembly of the first blade support arm(s) 103 pivoted to the second blade support arm(s) 107, without the cutting element 136 and blade arm 138, is referred to as the multi-arms assembly. As will be clear from the following description, the multi-arms assembly is used a number of times in the device 100, and the use of identical parts reduces manufacturing and inventory costs. Alternatively, the positioning arm support struts 103 and 107 could be sized differently but built in a similar manner as for the cutting assembly.

As seen in FIG. 14C (in a similar manner as described for device 10 in FIG. 4A), the leaflet cutting assembly 114 (which includes the cutting element 136 and blade arm 138) has one end pivotally coupled to opposite ends of a first biasing device 140 (which is part of the guiding structure 116) at pivot joints 142 and 146. The first biasing device 140 may be formed from or coupled with a distal slider tube 141. The first biasing device 140 provides, among other things, a safety feature: after using the device to cut tissue, the first biasing device 140 contracts to ensure that the assembly of the first blade support arm(s) 103 and the second blade support arm(s) 107 returns to the contracted state and does not protrude outwards and cannot harm nearby tissue. Thus, when contracted, the first biasing device 140 serves as a limiter that limits the amount the cutting element 136 can move radially outwards.

As seen in FIGS. 14D and 14E, a distal spring 121 may be mounted over distal slider tube 141. The leaflet cutting assembly 114 may be mounted in a frame 157 that has an open side 159. A frame plug 155 may be mounted on distal slider tube 141 between the distal end of frame 157 and the proximal end of distal spring 121.

As seen in FIG. 14F, leaflet support frame 112 includes a pair of multi-arms assemblies 119 pivotally coupled to first and second pivot joints 122 and 123 secured to a spacer frame tube 120 (which is part of the guiding structure 116). A second biasing device 150 is disposed on or part of spacer frame tube 120 and is located between first and second pivot joints 122 and 123. As with the first biasing device 140, the second biasing device 150 provides, among other things, a safety feature: after using the device to cut tissue, the second biasing device 150 contracts to ensure that the assembly of the first blade support arm(s) 103 and the second blade support arm(s) 107 returns to the contracted state and does not protrude outwards and cannot harm nearby tissue. Thus, when contracted, the second biasing device 150 serves as a limiter that limits the amount the positioning arms 103 and 107 of the multi-arms assemblies 119 can move radially outwards.

As seen in FIG. 14G, the multi-arms assemblies 119 and spacer frame tube 120 of leaflet support frame 112 are mounted in frame 157. A guide spring 160 may be mounted over the proximal end of spacer frame tube 120.

As seen in FIG. 14H, a strut arm 118, from which extends a blade protector 124, may be secured to the first blade support arm(s) 103 of multi-arms assembly 119 (the arm that is on the same side as opening 159). As with device 10, blade protector 124 may be shaped as a semi-hemispherical tube, and strut arm 118 and blade protector 124 may be collinear or may be tilted with respect to each other. A cable assembly 170, which may be made from a shape-memory alloy such as nitinol, may be coupled to the guiding structure 116 adjacent the distal end of distal spring 121. The cable assembly 170 can aid the distal spring 121 to collapse the cutting element 136 and the multi-arms assemblies 119 in the event of some difficulty in contraction of the assemblies.

Reference is made again to FIG. 14. The device 100 may be delivered to the surgical site with a sheath (not shown) covering the leaflet support frame 112 and the leaflet cutting assembly 114, so that device 100 is delivered as a slender tube-like structure. FIG. 14 shows device 100 after the sheath has been removed. This initially causes the blade protector 124 to expand (move) radially outwards, as shown in FIG. 14. In this initial position, the leaflet support frame 112 is axially spaced proximally from leaflet cutting assembly 114.

Reference is now made to FIG. 15. The guiding structure 116 (such as, but not limited to, a stainless steel or nitinol wire or tube) is moved distally so that the leaflet support frame 112 is moved distally towards leaflet cutting assembly 114. The distal end of leaflet support frame 112 (the distal arms 103) may abut against an abutment 99 formed at the distal end of opening 159 of frame 157. Abutment 99 may serve as a safety stop that limits the outward movement of blade protector 124. Note that the distal end portion of blade protector 124 is now positioned over the tip 137 of cutting element 136.

The spring force of the biasing devices 140 and 121 is greater than the spring force of the biasing devices 150 and 160 (such as a ratio of 2:1, although the invention is not limited to this ratio). As a result, the leaflet support frame 112 is expanded outwards before the leaflet cutting assembly 114 starts to expand outwards.

Figure 16:
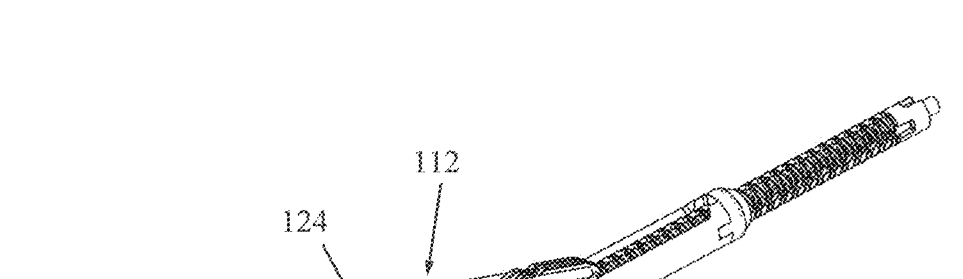
FIG. 16 is a simplified pictorial illustration of initial radially-outward expansion of the leaflet cutting assembly.
Figure 16:

Reference is now made to FIG. 16. Further distal movement of the guiding structure 116 starts to compress the first biasing device 140 and distal spring 121 (not seen here) so that the leaflet cutting assembly 114 starts to expand radially outwards.

Figure 17:
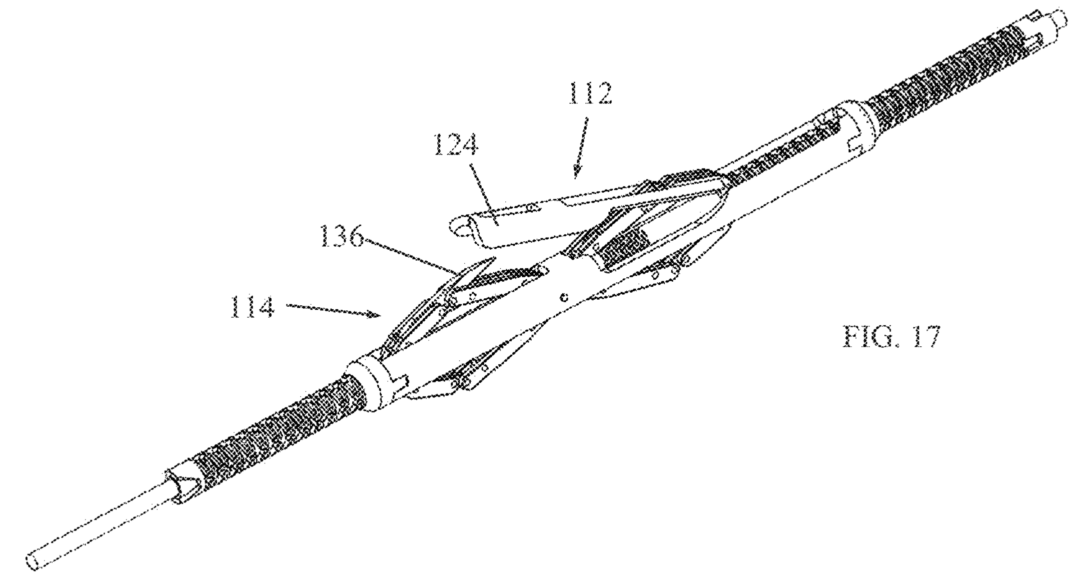
FIGS. 17 and 18 are simplified pictorial illustrations of further expansion of the leaflet cutting assembly so that finally the tip of the cutting element is close to the blade protector of the leaflet support frame.
Figure 18:
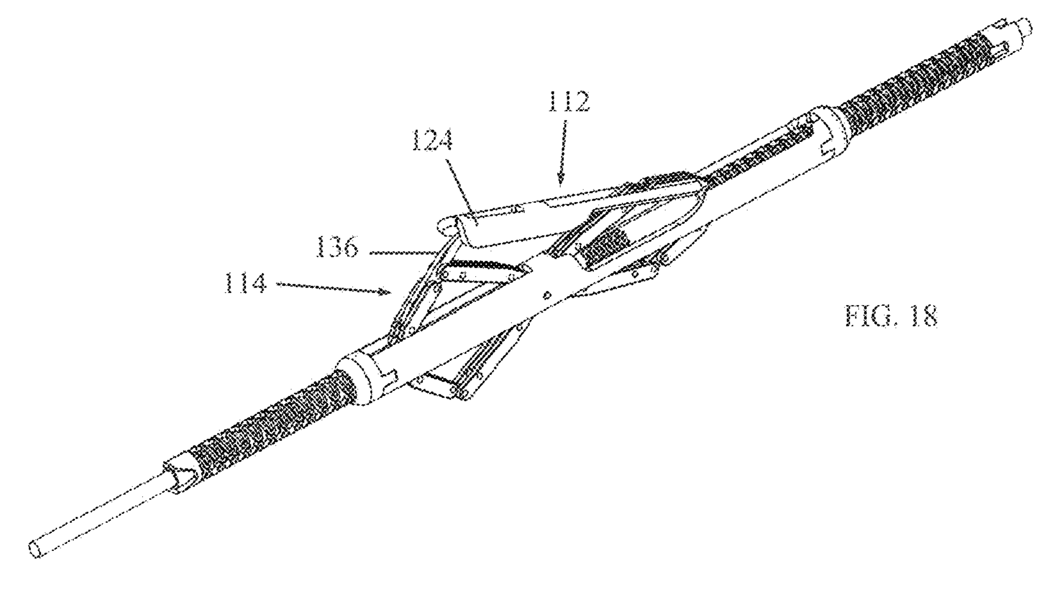

FIGS. 17 and 18 show further expansion of leaflet cutting assembly 114 so that finally the tip 137 of cutting element 136 is close to blade protector 124. The device 100 can be used to lacerate tissue as described for device 10.

Figure 19A:
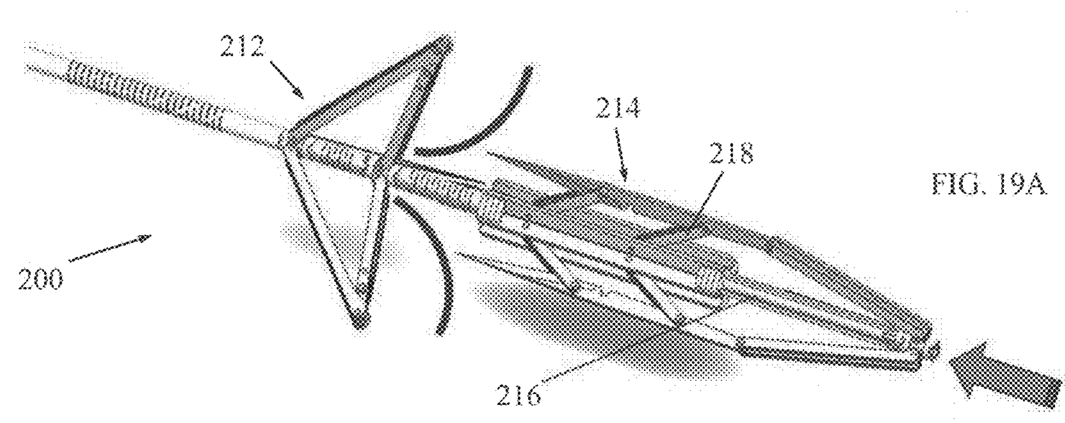
FIGS. 19A and 19B are simplified pictorial illustrations of a transcatheter valve laceration device, constructed and operative in accordance with another non-limiting embodiment of the invention, in respective collapsed and expanded orientations, in which the leaflet cutting assembly is constructed as a foldable hinged parallelogram.
Figure 19B:
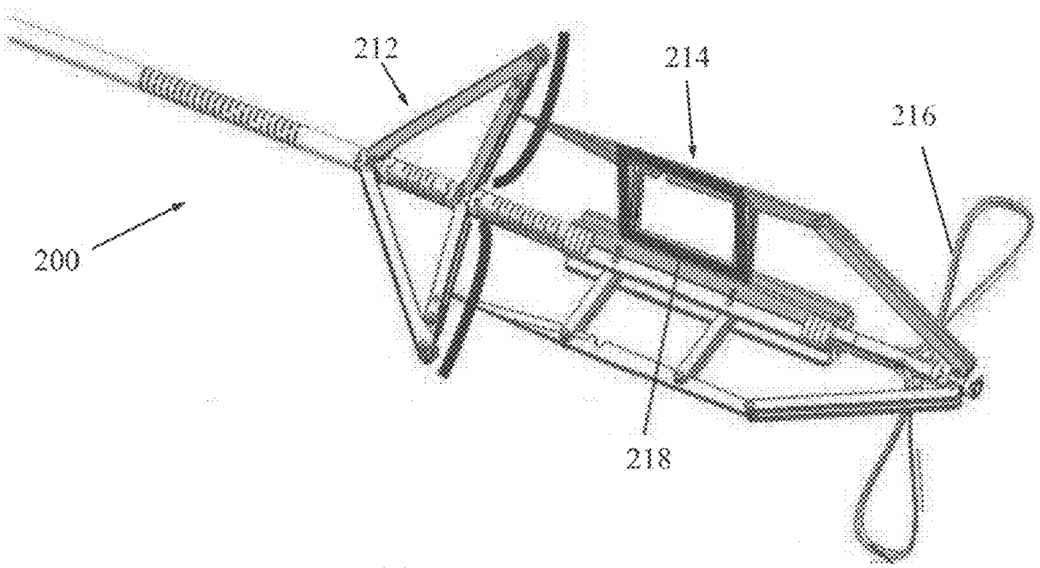

Reference is now made to FIGS. 19A and 19B, which illustrate a transcatheter valve laceration device 200, constructed and operative in accordance with another non-limiting embodiment of the invention. As with the other embodiments, device 200 includes a leaflet support frame 212 and a leaflet cutting assembly 214.

The leaflet cutting assembly 214 may be constructed as a foldable hinged parallelogram 218, in which axial movement is translated into radial motion to affect dissection of the leaflet.

The leaflet support frame 212 may be a triangular frame support structure, which supports the leaflet by self-positioning onto the valve cusps due to the geometry of the support members of the frame 212, which may be approximately 120° apart. The support frame construction allows blade penetration and alignment by ensuring that the blade passes through a double strut design of the frame. The blade punctures through the aortic valve leaflet and then dissects the leaflet by pressing it against the support frame 212 to create an anvil-like action.

The fully hinged mechanism allows folding of the mechanism to be sheathed into a delivery system catheter tube. Other embodiments may be based on other radial and non-radial flexing methods.

The cutting elements are constructed as a tri-lobe mechanism to allow simultaneous 120° positioning of all the leaflet cutting.

Activation of leaflet support frame 212 and leaflet cutting assembly 214 may be done by counter movement of two coaxial tubes.

A constant-force biasing device 216 (such as, but not limited to, a nitinol tube-based spring) may preload the blade or blades of the leaflet cutting assembly 214 mechanism in a normally closed or collapsed position. The biasing device 216 in its loaded position acts as a centering and radial support against the LVOT (left ventricular outflow tract) wall.

As with the other embodiments of the invention, leaflet puncturing may be performed from within the left ventricle with a circular movement of the blade tip towards the aorta to prevent damage to the aortic complex. The frame support allows for the cutting blade to dissect the leaflet at any desired location without exerting any forces on the leaflet annulus ring. The support frame deployment and positioning may be performed within the STJ (sinotubular junction) volume. An indicator, which may be placed on the activation handle, may indicate that the dissection action has been completed.

Mitral anterior leaflet laceration is performed for transcatheter mitral valve replacement (TMVR) procedure to prevent LVOT (left ventricle outflow tunnel) obstruction when the implant valve is positioned within the native valve of the patient.

The following procedure defines steps to use the above-described devices (referred to as the ShortCut™ device), to perform the procedure. The procedure may be performed on a transeptal access or transapical access implantation procedures, prior to the deployment of the implanted third-party valve.

The below steps define the procedure performed on a transapical access, but the invention is not limited to these particular steps. Similar actions could be performed on a transeptal access, for example, with the ShortCut™ device installed in a reversed orientation over the devices delivery system.

Procedure steps (clinical needs may require variations to the procedure and may be used to achieve the same goal):

1. Set echocardiogram (echo) viewing showing leaflets of the mitral valve.
2. Perform apical access procedure to insert an introducer sheath (e.g., a 16F introducer sheath) into the left ventricle.
3. Introduce a guidewire into the left atrium and insert the introducer sheath in between the mitral leaflets chordae, while not harming the pupillary muscles.
4. Introduce a ShortCut™ device through the introducer sheath and over the guidewire.
5. Unsheathe the device while in the introducer and verify direction of positioning arm (e.g., strut arm 118 and blade protector 124).
6. Advance the device through the introducer sheath into the atrium until the positioning arm has opened.
7. Verify that the positioning arm has opened in the required direction of laceration on the anterior leaflet.
8. Slowly retract the introducer sheath together with the cutting distal unit (e.g., leaflet cutting assembly 114 and cutting element 136), into the ventricle
9. Once the positioning arm has popped over the anterior leaflet advance the device towards the mitral valve annulus as close as possible to the aortic valve annulus.
10. Verify that the positioning arm is over the anterior leaflet and is positioned correctly in the A2 zone (middle of the anterior leaflet)
11. Activate the ShortCut™ splitting element (e.g., cutting element 136) and verify the positioning and full activation of the cutting mechanism.
12. Gradually apply a pull of the ShortCut™ system through the introducer sheath while inspecting the laceration by fluoroscopy and echo.
13. Once the leaflet has been lacerated, release the splitter mechanism.
14. Sheath the distal unit of the ShortCut™ device and retract it while verifying that the guidewire is safely positioned in the left atrium.

15. Remove the ShortCut™ device and exchange the introducer sheath with the recommended TMVR device sheath, over the guidewire.
16. Complete the TMVR device procedure and perform closure suturing of the apical puncture point.
17. Proceed with standard patient monitoring and caring procedure as required.

What is claimed is:

1. A method for lacerating heart tissue comprising:

using a device that comprises a leaflet support frame and a leaflet cutting assembly, both of which are movably mounted on a guiding structure and movable between contracted and expanded orientations, wherein said leaflet cutting assembly comprises a cutting element that comprises a sharp blade arm that has a pointed sharp tip at a distal end of said sharp blade arm, and a blade actuator arm pivotally coupled to said sharp blade arm, wherein in the expanded orientation, a blade protector of said leaflet support frame is positioned over said pointed sharp tip of said cutting element of said leaflet cutting assembly, introducing said device with said leaflet support frame and said leaflet cutting assembly in contracted orientations to a heart;

expanding said leaflet support frame;

expanding said leaflet cutting assembly; and moving said leaflet cutting assembly to lacerate heart tissue located between said cutting element and said blade protector.

2. The method according to claim 1, comprising first piercing said heart tissue with said pointed sharp tip of said cutting element of said leaflet cutting assembly prior to moving said leaflet cutting assembly to lacerate the heart tissue.

3. The method according to claim 1, comprising lacerating the heart tissue in a mitral anterior leaflet laceration procedure as part of a transcatheter mitral valve replacement (TMVR) procedure to prevent LVOT (left ventricle outflow tunnel) obstruction when an implant valve is positioned within a native valve of a patient.

4. The method according to claim 1, wherein said heart tissue comprises tissue of a mitral valve.

5. The method according to claim 1, wherein expanding said leaflet cutting assembly comprises one end of said blade actuator arm pivoting with respect to said guiding structure and an opposite end of said blade actuator arm pivoting with respect to said sharp blade arm proximal to said pointed sharp tip.

* * * * *